US00PP25743P3

(12) United States Plant Patent
Bradford

(10) Patent No.: US PP25,743 P3
(45) Date of Patent: Jul. 28, 2015

(54) APRICOT TREE NAMED 'GOLDEN GEM'

(50) Latin Name: *Prunus armeniaca*
Varietal Denomination: Golden Gem

(71) Applicant: Lowell Glen Bradford, Le Grand, CA (US)

(72) Inventor: Lowell Glen Bradford, Le Grand, CA (US)

( * ) Notice: Subject to any disclaimer, the term of this patent is extended or adjusted under 35 U.S.C. 154(b) by 91 days.

(21) Appl. No.: 13/998,863

(22) Filed: Dec. 16, 2013

(65) Prior Publication Data

US 2015/0173272 P1 Jun. 18, 2015

(51) Int. Cl.
*A01H 5/08* (2006.01)

(52) U.S. Cl.
USPC ..... Plt./186

(58) Field of Classification Search
USPC ..... Plt./156, 186
See application file for complete search history.

(56) References Cited

U.S. PATENT DOCUMENTS

PP8,932 P 10/1994 Bradford

*Primary Examiner* — Susan McCormick Ewoldt

(57) ABSTRACT

The present invention relates to a new and distinct variety of apricot tree, *Prunus armeniaca,* broadly characterized by a large size, vigorous, hardy, mid to late seasonal blooming, self-fertile, productive and regular bearing tree. The fruit matures under the ecological conditions described in early June, with first picking on Jun. 6, 2013. The fruit is uniformly medium in size, mildly acidic and sweet in flavor, nearly globose in shape, freestone in type, firm and meaty in texture, orange yellow in flesh color, and orange yellow with some red blush in skin color.

1 Drawing Sheet

Botanical classification: *Prunus armeniaca.*
Variety denomination: 'GOLDEN GEM'.

BACKGROUND OF THE VARIETY

In a continuing effort to improve the quality of shipping fruits, I, the inventor, typically hybridize a large number of apricot, nectarine, plum, apricot, and cherry seedlings each year. I also grow a lesser number of open pollinated seeds of each of these fruits, usually to capture recessive traits. The present invention relates to a new and distinct variety of apricot tree, which has been denominated varietally as 'Golden Gem'.

The present variety was hybridized by me in 2001 as a first generation cross using an unnamed apricot tree as the selected seed parent and '34P34' (unpatented) apricot as the selected pollen parent. The fruit of this cross was gathered that spring, and the seeds were removed, cracked, stratified, germinated, and grown as seedlings on their own root in my greenhouse. Upon reaching dormancy the seedlings were transplanted as a group to a cultivated area of my experimental orchard located near Le Grand, Calif., in Merced County (San Joaquin Valley). During the fruit evaluation season of 2005 I selected the present variety as a single tree from the group of seedlings described above. Subsequent to origination of the present variety of apricot tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its pollen parent, '34P34,' by producing fruit that ripens in the mid to late season and that is good in flavor, but is distinguished therefrom by being self-fruitful, by being more productive, and by producing fruit that is firmer in texture.

The present variety is most similar to Goldensweet (U.S. Plant Pat. No. 8,932) apricot by being self-fruitful and productive, but is distinguished therefrom by blooming about five days earlier and by producing fruit that is somewhat larger in size, that has a deeper orange yellow skin coloration, and that matures about five days earlier.

SUMMARY OF VARIETY

In summary, the present variety is characterized by a large size, vigorous, hardy, mid to late seasonal blooming, self-fertile, productive and regular bearing tree. The fruit matures under the ecological conditions described in early June, with first picking on Jun. 6, 2013. The fruit is uniformly medium in size, mildly acidic and sweet in flavor, nearly globose in shape, freestone in type, firm and meaty in texture, orange yellow in flesh color, and orange yellow with some red blush in skin color.

DRAWING

The accompanying photograph consists of four whole fruits positioned to display the characteristics of the skin color and form, one fruit divided to reveal the flesh and stone, typical leaves, and a tip shoot.

POMOLOGICAL CHARACTERISTICS

Referring now more specifically to the pomological characteristics of this new and distinct variety of apricot tree, the following has been observed under the ecological conditions prevailing near Le Grand, Merced County (San Joaquin Valley), Calif., and was developed at the state of firm ripe on Jun. 12, 2013, on the original tree during its twelfth growing season. The blossom and flower descriptions were made the previous blooming season. All major color code designations are by reference to the Inter-Society Color Council, National Bureau of Standards. Common color names are also used occasionally.

PARENTAGE

Seed parent: Unnamed apricot tree.
Pollen parent: '34P34 (unpatented) apricot tree.

TREE

Size: Large, reaching and maintaining a height of 14' [4.27 m.] and a spread of 15' [4.57 m.] after twelve growing seasons utilizing typical dormant pruning.
Vigor: Vigorous, responding typically to irrigation and fertilization. The variety grows about 3' [0.91 m.] of surplus top-growth during the spring and summer. The plant should be grown on a standard commercial rootstock for production purposes.
Growth: Spreading and dense.
Form: Vase type.
Hardiness: Hardy with respect to central California winters.
Heat tolerance: Observed to perform adequately in typical central California climatic conditions, which typically include extended periods of heat.
Drought tolerance: Variety is developed for commercial orchards and requires regular irrigation.
Production: Productive, thinning necessary.
Fertility: Self-fertile.
Bearing: Regular bearer with no alternate bearing yet observed.
Trunk:
- *Size.*—Large, reaching a maximum diameter of 7" [177.8 mm.] after the twelfth growing season.
- *Texture.*—Medium shaggy.
- *Bark color.*—A Light grayish brown [60. l.gy.Br] and Grayish brown [61. gy.Br] variegation with Brownish orange [54. brO] crevices present.
- *Lenticels.*—Approximate Number Per Square Inch: 6. Color: Light yellowish brown [76. l.yBr]. Average Size: 3/16" [4.8 mm.]. Shape: Eye-shaped, elongated.

Branches:
- *Size.*—Diameter of main scaffold is 4" [102 mm.] measured 12" above the crotch, diameter of limb is 1¼" [32 mm.] measured 12" above the first fork.
- *Texture.*—Smooth on first and second year wood, increasing roughness with age.
- *Color.*—1st Year Wood Topside: Strong yellow green [117. s.YG]. 1st Year Wood Underside: Brownish orange [54. brO]. Older Wood: A Grayish brown [61. gy.Br] with Dark grayish brown [62. d.gy.Br] variegation and Light brownish gray [63. l.brGy] crevices present.
- *Lenticels.*—Number Per Square Inch: About 25 on second year wood. Color: Light yellowish brown [76. l.yBr]. Average size: 1/16" [1.6 mm.] on second year wood. Shape: Elongated.

Leaves:
- *Size.*—Medium. Average Length: 2¾" [69.9 mm.]. Average Width: 2½" [63.5 mm.].
- *Arrangement.*—Alternate.
- *Thickness.*—Medium.
- *Form.*—Oval to orbicular.
- *Apex.*—Abruptly acuminate.
- *Base.*—Rounded.
- *Surface.*—Smooth.
- *Color.*—Dorsal Surface: Moderate olive green [125. m.OlG]. Ventral Surface: Deep yellow green [118. deep YG].
- *Margin.*—Finely serrate.
- *Venation.*—Pinnately net veined.
- *Vein color.*—Brilliant yellow green [116. brill.YG].
- *Petiole.*—Average Length: 1" [25.4 mm.]. Average Thickness: 1/16" [1.6 mm.]. Color: Pale yellow green [121. p.YG] topside, Strong yellow green [117. s.YG] underneath.
- *Stipules.*—Number: Usually 2 per leaf, up to 6 per growing tip. Average Length: Very short, ⅛" [3.2 mm.]. Color: Dark olive green [126. d.OlG].
- *Glands.*—Average Number: 4 per leaf. Position: Occurring in slightly alternate pairs positioned on petiole and base of blade. Size: Medium to small. Form: Globose. Color: Dark grayish olive green [128. d.gy. OlG].
- *Leaf buds.*—Pointed, medium in size.

Flower buds:
- *Hardiness.*—Hardy, with respect to central California winters.
- *Diameter.*—Typically 5/16" [7.9 mm.] 5 days before bloom.
- *Length.*—Typically ⅜" [9.5 mm.] 5 days before bloom.
- *Form.*—Not appressed.
- *Surface.*—Pubescent.
- *Color.*—Light purplish pink [249. l.pPk].

Flowers: Perfect, complete, perigynous, usually a single pistil, typically about twenty-four stamens, five sepals and petal locations alternately positioned.
- *Average flower diameter.*—1¼" [31.8 mm.].
- *Number of petals.*—Usually five.
- *Petal shape.*—Circular to elliptical.
- *Petal margin.*—Entire, fairly smooth.
- *Average petal diameter.*—½" [12.7 mm.].
- *Average petal length.*—½" [12.7 mm.].
- *Petal apex.*—Rounded.
- *Petal base.*—Rounded.
- *Petal color.*—Pale pink [7. p.Pk] on both sides.
- *Anther color.*—Brilliant yellow [83. brill.Y].
- *Stigma color.*—Light greenish yellow [101. l.gY].
- *Sepal color.*—Dark purplish red [259. d.pR] on the outer surface.
- *Sepal length.*—9/32" [7.1 mm.].
- *Sepal width.*—3/16" [4.8 mm.].
- *Sepal apex.*—Rounded to acute.
- *Sepal margin.*—Smooth.
- *Average pistil length.*—½" [12.7 mm.].
- *Average stamen length.*—7/16" [11.1 mm.].
- *Fragrance.*—Moderate.
- *Pollen production.*—Abundant.
- *Blooming period.*—Mid to late compared to other apricots, nine days after 'Goldenmay' (U.S. Plant Pat. No. 20,104).
- *Onset of bloom.*—One percent on Mar. 1, 2013.
- *Date of full bloom.*—Mar. 8, 2013.
- *Duration of bloom.*—One to two weeks, dependent on ambient temperature.
- *Average number per cluster.*—Three.

FRUIT

Maturity when described: Firm ripe, Jun. 12, 2013.
Date of first picking: Jun. 6, 2013.
Date of last picking: Jun. 16, 2013.
Size: Uniform, medium.
*Average diameter axially.*—2⅛" [54.0 mm.].
*Average diameter across suture plane.*—2⅛" [54.0 mm.].
*Average diameter across cheek plane.*—2" [50.8 mm.].
*Typical weight.*—2.9 ounces [82 grams].
Form: Uniform, globose to slightly oblong, slightly asymmetrical, compressed laterally.
*Longitudinal section form.*—Round.
*Transverse section through diameter.*—Elliptical.
Suture: Extends from the base, along the side, just to the apex.
*Near the base.*—A sharp groove.
*Along the side.*—Shallow trough.
*Near the apex.*—A shallow groove with a slight depression just beyond the pistil point.
Ventral surface: Rounded, slightly lipped toward the apex.
Lips: Slightly unequal.
Cavity: Flaring, elongated in suture plane, suture showing on both sides.
*Depth.*—5/16" [7.9 mm.].
*Breadth.*—¾" [19.1 mm.].
Base: Truncate, slightly cordate if viewed parallel to the suture.
Apex: Rounded to slightly truncate.
Pistil point: An inconspicuous Grayish reddish brown [46. gy.rBr] dot, negligible in length, recessed within the suture.
Stem: Medium.
*Average length.*—⅜" [9.5 mm.].
*Average width.*—3/32" [2.4 mm.].
Skin:
*Thickness.*—Medium.
*Surface.*—Pubescent.
*Tenacity.*—Tenacious to flesh.
*Astringency.*—Slightly astringent.
*Tendency to crack.*—None observed in dry season.
*Color.*—Very orange yellow [66. v.OY] smoothly blending into a Deep orange yellow [69. deep OY] background with some Very reddish orange [34. v.rO] blush where exposed to direct sunlight.
Flesh:
*Color.*—Deep orange yellow [69. deep OY] becoming Strong orange yellow [68. s.OY] with increasing maturity.
*Surface of pit cavity.*—Covered with Moderate orange yellow [71. m.OY] fibers.
*Amygdalin.*—Moderate.
*Juice.*—Abundant, rich.
*Texture.*—Firm, tough, melting.
*Fibers.*—Abundant, fine.
*Ripens.*—Fairly even.
*Flavor.*—A mild balance of acid and sugar, typically 17 brix.
*Aroma.*—Slight.
*Eating quality.*—Very good.

STONE

Type: Freestone.
Form: Oval.
Hilum: Narrow, oblong.
Base: Rounded.
Apex: Rounded.
Sides: Equal.
Surface: Rough throughout.
External color of stone: Dark yellowish brown [78. d.yBr].
Pit wall color when cracked: Moderate yellowish brown [77. m.yBr].
Cavity surface color: A Light yellowish brown [76. l.yBr].
Average pit wall thickness: 1/16" [1.6 mm.].
Average width: ⅞" [22.2 mm.].
Average length: 1 1/16" [27 mm.].
Average breadth: ½" [12.7 mm.].
Tendency to split: None observed.
Kernel:
*Form.*—Oval.
*Skin color.*—Strong yellowish brown [74. s.yBr].
*Pellicle color.*—Light grayish yellowish brown [79. l.gy.yBr].
*Taste.*—Bitter.
*Viable.*—Yes.
*Average width.*—½" [12.7 mm.].
*Average length.*—13/16" [20.6 mm.].
*Amygdalin.*—Abundant.

USE

Market: Fresh market and long distance shipping.
Keeping quality: Good, fruit quality observed to remain in good condition after 14 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of apricot tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of apricot tree, substantially as illustrated and described, that is most similar to Goldensweet (U.S. Plant Pat. No. 8,932) apricot by being self-fruitful and productive, but is distinguished therefrom by blooming about five days earlier and by producing fruit that is somewhat larger in size, that has a deeper orange yellow skin coloration, and that matures about five days earlier.

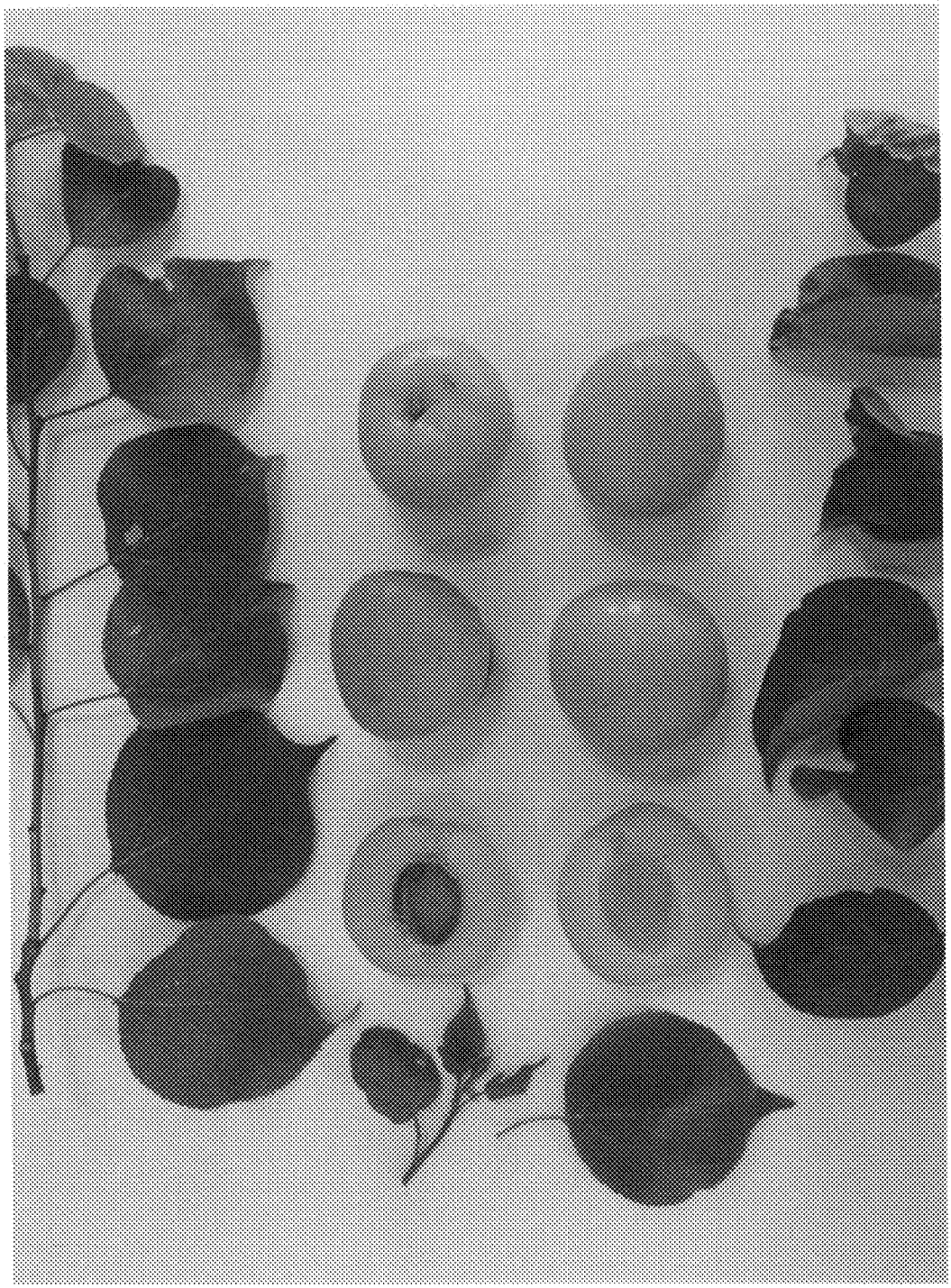

* * * * *